United States Patent [19]

Clark

[11] Patent Number: 5,726,010

[45] Date of Patent: Mar. 10, 1998

[54] REVERSIBLE FLOW CHROMATOGRAPHIC BINDING ASSAY

[75] Inventor: Scott M. Clark, Cape Elizabeth, Me.

[73] Assignee: IDEXX Laboratories, Inc., Westbrook, Me.

[21] Appl. No.: 738,321

[22] Filed: Jul. 31, 1991

[51] Int. Cl.$^6$ .................. G01N 33/569; G01N 33/543; G01N 33/558

[52] U.S. Cl. .................. 435/5; 422/55; 422/56; 422/57; 422/58; 435/7.71; 435/287.1; 435/287.2; 435/805; 435/810; 435/970; 436/165; 436/169; 436/514; 436/518; 436/528; 436/530; 436/531; 436/805; 436/807; 436/808; 436/809; 436/810

[58] Field of Search .................. 435/5, 7.71, 287.1, 435/287.2, 805, 970, 810; 436/518, 528, 530, 531, 165, 169, 805, 514, 807–810; 422/55–58

[56] References Cited

U.S. PATENT DOCUMENTS

| | | |
|---|---|---|
| 3,615,222 | 10/1971 | Mead . |
| 3,645,687 | 2/1972 | Nerenberg .................. 195/139 LE |
| 3,715,192 | 2/1973 | Wenz et al. .................. 23/253 TP |
| 3,799,742 | 3/1974 | Coleman .................. 23/253 R |
| 3,811,840 | 5/1974 | Bauer et al. .................. 23/253 TP |
| 3,825,410 | 7/1974 | Bagshawe .................. 23/259 |
| 3,843,324 | 10/1974 | Edelman et al. .................. 23/230 B |

(List continued on next page.)

FOREIGN PATENT DOCUMENTS

| | | |
|---|---|---|
| 1 211 157 | 9/1986 | Canada . |
| 0 297 292 | 5/1988 | European Pat. Off. . |
| 0 309 883 | 9/1988 | European Pat. Off. . |
| 0 322 340 | 12/1988 | European Pat. Off. . |

(List continued on next page.)

OTHER PUBLICATIONS

Henning et al., *Proc. Natl. Acad. Sci. USA*, 76:4360–4364, 1979.

Renart et al., *Proc. Natl. Acad. Sci. USA*, 76:3116–3120, 1979.

Pappas et al., *Journal of Immunological Methods*, 64:205–214, 1983.

Holmberg et al., *Journal of Immunological Methods*, 61:9–6, 1983.

Jalkanen et al., *J. Clin. Lab. Immunol.*, 10:225–228, 1983.

Hawkes, *Analytical Biochemistry*, 123:143–146, 1982.

(List continued on next page.)

Primary Examiner—Christopher L. Chin
Attorney, Agent, or Firm—Fish & Richardson P.C.

[57] ABSTRACT

Disclosed are devices and methods for performing an assay which determines the presence or quantity of an analyte in a fluid sample by detecting binding of the analyte to at least one immobilized analyte capture reagent and washing unbound material from the immobilized analyte capture reagent. The devices and methods an elongated solid phase flow matrix, including capillary channels capable of driving capillary fluid movement, and further including (i) a first region adapted for receipt of the fluid sample, (ii) a second region at which the analyte capture reagent is immobilized, (iii) a third region for application of a wash reagent capable of removing unbound substances from the second region; and (iv) an absorbent reservoir of high volume capacity. The second region is positioned intermediate to the first region and the third region and intermediate to the absorbent reservoir and the third region. The device also includes means to detect analyte bound at the second region. The flow matrix and the regions thereof are sized and positioned to cause the fluid sample to flow initially along the elongated flow matrix in one direction toward and through the second region, and subsequently, the liquid reagent to flow along the elongated flow matrix in a second direction opposite the first direction, through the second region, and into the absorbent reservoir, drawing unbound substances with it.

36 Claims, 1 Drawing Sheet

U.S. PATENT DOCUMENTS

| | | | |
|---|---|---|---|
| 3,888,629 | 6/1975 | Bagshawe . | |
| 3,966,897 | 6/1976 | Renn et al. | 424/8 |
| 4,039,652 | 8/1977 | Adams et al. | 424/1 |
| 4,053,284 | 10/1977 | Posh . | |
| 4,056,284 | 11/1977 | Posch | 424/1 |
| 4,061,468 | 12/1977 | Lange et al. | 428/535 |
| 4,088,448 | 5/1978 | Lija et al. | 356/246 |
| 4,094,647 | 6/1978 | Deutsch et al. | 23/230.3 |
| 4,125,372 | 11/1978 | Kawai et al. | 422/56 |
| 4,138,474 | 2/1979 | Updike | 422/58 |
| 4,153,675 | 5/1979 | Kleinerman | 422/56 |
| 4,168,146 | 9/1979 | Grubb et al. . | |
| 4,180,383 | 12/1979 | Johnson . | |
| 4,193,983 | 3/1980 | Ullman et al. | 435/188 |
| 4,200,690 | 4/1980 | Root et al. | 435/28 |
| 4,233,029 | 11/1980 | Columbus . | |
| 4,235,601 | 11/1980 | Deutsch et al. | 422/56 |
| 4,246,339 | 1/1981 | Cole et al. | 422/161 |
| 4,275,149 | 6/1981 | Litman et al. | 435/177 |
| 4,277,560 | 7/1981 | Gray et al. | 422/81 |
| 4,298,685 | 11/1981 | Parikh et al. | 435/188 |
| 4,305,924 | 12/1981 | Piasio et al. | 422/61 |
| 4,318,980 | 3/1982 | Boguslaski et al. | 435/188 |
| 4,322,495 | 3/1982 | Kato | 435/810 |
| 4,358,535 | 11/1982 | Falkow et al. | 435/5 |
| 4,366,241 | 12/1982 | Tom et al. | 435/810 |
| 4,376,110 | 3/1983 | David et al. | 436/513 |
| 4,391,904 | 7/1983 | Litman et al. | 435/188 |
| 4,424,279 | 1/1984 | Bohn et al. | 422/61 |
| 4,425,438 | 1/1984 | Bauman et al. . | |
| 4,426,451 | 1/1984 | Columbus . | |
| 4,427,769 | 1/1984 | Adlercruetz et al. | 422/61 |
| 4,435,504 | 3/1984 | Zuk et al. | 435/805 |
| 4,446,869 | 5/1984 | Knodle | 128/207.18 |
| 4,587,102 | 5/1986 | Nagatomo et al. . | |
| 4,717,656 | 1/1988 | Swanljung . | |
| 4,740,468 | 4/1988 | Wong et al. . | |
| 4,756,884 | 7/1988 | Hillman et al. | 435/810 |
| 4,774,177 | 9/1988 | Marks | 435/7.95 |
| 4,826,759 | 5/1989 | Guire et al. | 435/4 |
| 4,839,275 | 6/1989 | Weil . | |
| 4,906,439 | 3/1990 | Grenner . | |
| 4,918,025 | 4/1990 | Grenner | 436/165 |
| 4,923,680 | 5/1990 | Nelson | 422/61 |
| 4,956,302 | 9/1990 | Gordon et al. | 436/161 |
| 4,963,498 | 10/1990 | Hillman et al. . | |
| 5,051,237 | 9/1991 | Grenner et al. . | |
| 5,104,793 | 4/1992 | Buch | 436/518 |
| 5,104,812 | 4/1992 | Kum et al. . | |
| 5,141,850 | 8/1992 | Cole et al. . | |

FOREIGN PATENT DOCUMENTS

| | | |
|---|---|---|
| 2204398 | 11/1988 | United Kingdom . |
| WO 87/02774 | 5/1987 | WIPO . |
| WO 86/06488 | 11/1988 | WIPO . |
| WO 88/08534 | 11/1988 | WIPO . |
| WO 91/12528 | 8/1991 | WIPO . |
| WO 91/15769 | 10/1991 | WIPO . |
| WO 92/21977 | 12/1992 | WIPO . |

OTHER PUBLICATIONS

Cleveland et al., *Journal of Immunological Methods*, 29:369–386, 1979.

Towbin et al., *Proc. Natl. Acad. Sci. USA*, 76:4350–4354, 1979.

Dafforn et al., *Clin. Chem.*, 36:1312–1316, 1990.

Li et al., *Analytical Biochemistry*, 166:276–283, 1987.

Zuk et al., *Clin. Chem.*, 31:1144–1150, 1985.

Towbin et al., *Journal of Immunological Methods*, 72:313–430, 1984.

REVERSIBLE FLOW CHROMATOGRAPHIC BINDING ASSAY

BACKGROUND OF THE INVENTION

The invention relates to methods and devices for performing specific binding assays, in particular, for detecting the presence of an analyte in a fluid sample.

Detection of a particular analyte (e.g., an antigen, such as a pathogen or a hormone or a single-stranded nucleic acid target) in a fluid sample may be accomplished using a variety of binding assays, e.g., immunoassays or DNA hybridization assays. Generally, such an assay involves reaction of the test sample with a specific binding reagent (e.g., a specific antibody) and with a reagent which facilitates the direct or indirect quantitative measurement of the amount of the analyte of interest in the test sample. In one particular example known as an Enzyme-linked Immunosorbent Assay or ELISA, an antibody covalently bound to an enzyme (e.g., horseradish peroxidase) is reacted with a test sample and the presence of an analyte is assayed by reaction of the immunocomplex with substrate (e.g., 4-chloro-1-naphthol) followed by measurement of the colored end product.

Coleman (U.S. Pat. No. 3,799,742; 1974) reports an immunoassay which involves the breaking of two membranes to allow a fluid sample to flow into a chamber containing specific binding reagents (e.g., an antibody specific for the analyte). The presence of the analyte is monitored by a color reaction.

Bauer et al. (U.S. Pat. No. 3,811,840; 1974) report the use of specific binding reagents immobilized on an absorbent wick. The wick is dipped into an analyte-containing sample, facilitating the migration of the sample into the wick; the presence of analyte is detected by a color reaction.

Neremberg (U.S. Pat. No. 3,645,687; 1972) reports an immunoassay similar to that of Bauer et al., except that the analyte-containing sample is applied with a capillary tube.

Dafforn et al. (*Clin. Chem.* 36:1312, 1990) report an immunoassay for HIV antibody detection. Latex microspheres coated with antigen are embedded in the fibers of a wick; a human serum sample, applied to the wick, migrates downstream (by capillary action) contacting the antigen. Crushing of a substrate ampule releases substrate into a sponge (located upstream of the sample entry port). When saturated, the sponge expands to contact the wick, and substrate is slowly transported into the wick. Simultaneous to substrate release, a protein-A-enzyme conjugate solution is manually added to the wick downstream of the sample entry port. Slow release of the substrate by the sponge allows time for conjugate reaction with the immobilized antibody-antigen complex. Complexes are detected by color reaction.

Li et al. (*Analytical Biochem.* 166:276, 1987) report a one-step immunoassay in which a paper support containing immobilized antibodies and enzyme is dipped into a sample containing substrate, a color indicator, and an enzyme inhibitor, as well as the analyte to be detected. Capillary action draws the sample up the paper, the inhibitor (present in a finite quantity) migrates out of the reactive zone, and color development is assayed. The height of the color bar is proportional to the analyte concentration.

Zuk et al. (U.S. Pat. No. 4,435,504; 1984 and *Clin. Chem.* 31:1144, 1985) report a competitive immunoassay using a dry paper strip containing immobilized antibody. The strip is dipped first into a solution containing both the analyte and an enzyme-analyte conjugate and then completely immersed into a solution containing substrate and a color developer. The height of the color bar is proportional to the analyte concentration.

Deutsch et al. (U.S. Pat. No. 4,094,647; 1980) report a competitive immunoassay in which a sample analyte is blotted onto an absorbent test strip. The strip is dipped into a developing fluid which transports the analyte along the test strip (by capillary action), facilitating contact first with labelled analyte and then with immobilized analyte-specific antibody. Unbound reagents are transported farther along the test strip. Labelled analyte and sample analyte compete for binding to the immobilized antibody; the amount of label measured at the site of immobilized antibody is inversely proportional to the quantity of analyte in the sample.

Cole et al. (U.S. Pat. No. 3,246,339; 1981) report the use of an absorbent reservoir to draw off excess liquid from the test wells of an assay device; analyte is trapped on the test wells' porous membrane surface and detected.

Bagshawe (U.S. Pat. No. 3,888,629; 1975) report the use of an absorbent reservoir to promote filtration of a fluid sample through a matrix pad containing dried specific binding reagent.

Tom et al. ((U.S. Pat. No. 4,366,241) reports an immunoassay device having two bibulous zones, an analyte binding partner being non-diffusively fixed in a first zone (the "immunoabsorbing zone"), and the second zone being a reservoir zone which is either directly or indirectly in liquid-receiving relationship with the first zone to pull liquid through and out of the first zone.

Brooks et al. (WO90/05906) reports a test device which includes (i) a reaction zone capable of retaining a detectable assay product, (ii) a control absorbent in liquid-transferring contact with the reaction zone which meters a predetermined flow of sample or binding reagents through the reaction zone, and (iii) an absorbent reservoir which speeds flow of fluid through the control absorbent.

SUMMARY OF THE INVENTION

The instant invention makes use of bi-directional capillary flow (i.e., reversible flow) to transport an analyte-containing sample first in one direction and then in the opposite direction along an elongated capillary flow matrix. Such reversible flow makes more efficient use of available sample by maximizing analyte contact with specific binding reagents (i.e., both during forward flow and during reverse flow). Reversible flow also facilitates elimination of unreacted sample and unbound reagents from the detection zone; a detector/wash reagent is flowed along the assay device in the opposite direction to the original sample flow drawing with it unbound or unreacted constituents. This increases the sensitivity of the assay by removing reagents which contribute to non-specific background. Such advantages (described in detail below) are provided by the assay devices and methods of the instant invention.

In general, a first aspect of the invention features a device for performing an assay which determines the presence or quantity of an analyte (e.g., a viral antigen, preferably a feline leukemia virus or a human immunodeficiency virus, or, alternatively, a canine heartworm antigen, e.g., an antigen derived from *Dirofilaria immitis*) in a fluid sample by detecting binding of the analyte to at least one immobilized analyte capture reagent. To facilitate detection, unbound material is washed from the immobilized analyte capture reagent zone. The device involves an elongated solid phase flow matrix which includes capillary channels capable of driving capillary fluid movement and means to detect analyte bound at the second region. The flow matrix itself includes the following regions: (i) a first region adapted for receipt of the fluid sample, (ii) a second region at which the analyte capture reagent is immobilized, (iii) a third region for application of a liquid reagent capable of removing unbound substances from the second region; and (iv) an absorbent reservoir that has a high volume of absorbent capacity. The second region is positioned intermediate to the first region and the third region and intermediate to the absorbent reservoir and the third region. The flow matrix and the regions thereof are sized and positioned to cause the fluid sample to flow initially along the elongated flow matrix in one direction toward and through the second region, and subsequently, to cause the liquid reagent to flow along the elongated flow matrix in a second direction opposite the first direction, through the second region, and into the absorbent reservoir, drawing unbound substances with it.

In a first preferred embodiment, the means to detect analyte bound at the second region involves a reagent which undergoes a detectable reaction, and the liquid reagent includes a predetermined limited quantity of an inhibitor of the detectable reaction, together with an excess of at least one of the other reagents that participates in the reaction. In a device according to this embodiment, flow of the liquid reagent transports the inhibitor initially to the second region, and, once the inhibitor and unbound substances have been transported away from the second region, the detectable reaction takes place in the absence of the unbound substances.

In a second preferred embodiment, the device includes liquid reagent in a sealed container and means (preferably, a lance) for applying the liquid reagent to the third region of the matrix (preferably by piercing the container).

In a third preferred embodiment, the absorbent reservoir is positioned (prior to use) so as not to contact the flow matrix, and means are included in the device for moving the absorbent reservoir into fluidic contact with the flow matrix. In addition, the means for applying the liquid reagent to the third region may be connected to the means for moving the absorbent reservoir into contact with the flow matrix, allowing an operator to activate both mechanisms in a single operation.

In a fourth preferred embodiment, the liquid reagent applied at the third region is a wash reagent and the flow matrix further includes a fourth region for the application of a detector reagent; the third region is positioned intermediate to the second region and the fourth region so that wash reagent is delivered to the second region (facilitating removal of unbound sample and unreacted liquid reagents) prior to delivery of the detector reagent. A device according to this embodiment may include a sealed detector reagent storage container and a sealed wash reagent storage container positioned adjacent to the fourth region of the flow matrix. In addition, the detector reagent application means may be connected to the wash reagent application means (for example, a lance positioned and adapted to pierce both containers), so that an operator may apply both reagents in a single operation.

Finally, in a fifth preferred embodiment, the device involves at least one barrier which includes a soluble member positioned to block flow of the liquid reagent (e.g. wash or detector reagent) to the absorbent reservoir. After a predetermined time selected to be sufficient to permit the sample to flow in the first direction through the second region, dissolution of the solid member permits fluid flow of the liquid reagent in the second direction to the absorbent reservoir. Preferably, such a barrier is positioned either between the first region and the absorbent reservoir; between the third region and the second region; or both.

In a second aspect, the invention features methods for performing an assay of the type described above. Such methods involve: (a) providing one of the above-described devices; applying the fluid sample to the flow matrix of the device; and detecting the analyte bound at the second region of the flow matrix.

The various preferred embodiments of the first aspect of the invention are used in performing preferred methods according to the second aspect of the invention.

In a final aspect, the invention features a device for performing an assay of the type described above which involves an elongated fluid flow matrix including a first segment for receiving a fluid sample, a second region at which analyte capture reagents are immobilized, an absorbent reservoir, a supply of liquid reagent, and a soluble barrier positioned to block flow in the matrix. The second region is positioned intermediate to the supply of liquid reagent and the absorbent reservoir. The soluble barrier is positioned to prevent flow of the liquid reagent from the supply to the absorbent reservoir until after the sample has flowed from the first region through the second region. At that point, the barrier dissolves permitting the wash reagent to flow through the second region and into the absorbent reservoir.

In preferred embodiments, a barrier is positioned either between the liquid reagent and the second region; or between the first region and the absorbent reservoir; or both.

By "analyte" is meant the molecule to be detected. For example, an analyte, as used herein, may be a ligand, which is mono- or polyepitopic, antigenic or haptenic; it may be a single compound or plurality of compounds which share at least one common epitopic site; it may also be a receptor or an antibody.

By "immobilized analyte capture reagent" is meant a molecule which is bound to a solid support and which has a specific affinity for an analyte of interest. Preferably, the affinity arises by virtue of the reagent possessing a complementary three-dimensional structure to the analyte, e.g., as seen in the relationship between an enzyme and a substrate or an antigen and an antibody. Within a given pair, either member may be considered to be the analyte or the capture reagent. The definition serves only to differentiate the component to be detected in the sample (i.e., the analyte) from the reagent included in the device or method (i.e., the analyte capture reagent).

Examples of analyte:analyte capture reagent pairs include, without limitation, all of the following combinations: a pathogen (e.g., a bacteria, virus, fungus, filarial parasite, or protozoan); a soluble protein (e.g., a growth factor, a lymphokine, a toxin, or a hormone); or a cell-surface protein or carbohydrate (e.g., a cell adhesion molecule, a laminin, a fibronectin, an integrin, or a lectin) and a specific antibody or a specific receptor. Such a pair may also include drugs, metabolites, pesticides, or pollutants and receptors specific to each.

By "absorbent reservoir of high volume capacity" is meant an absorbent reservoir, e.g., an absorbent pad, which is capable of accommodating a volume of liquid in excess of the total volume of sample and the total volume of all added liquid reagents (e.g., detector reagent or wash reagent).

By "lance" is meant a component which is capable of piercing the seal of a liquid reagent container. Such a lance may also include a wick which facilitates flow of the liquid reagents out of their storage container and into the flow matrix.

By "liquid reagent" is meant a fluid which transports unbound material (e.g., unreacted fluid sample and unbound specific binding reagents) away from the second region. The liquid reagent may be a "wash reagent" and serve only to remove unbound material from the second region, or it may include a "detector reagent" and serve to both remove unbound material from the second region and to facilitate analyte detection. The liquid reagent may further include a limited quantity of an "inhibitor", i.e., a substance which blocks the development of the detectable end product. By "limited quantity" is meant an amount of inhibitor sufficient to block end product development until most or all excess, unbound material is transported away from the second region, at which time detectable end product is produced.

The methods and devices of the present invention provide a number of advantages. For example, devices and methods according to the invention facilitate unusually sensitive analyte detection. Sample liquid is flowed within the device in such a manner that analyte is in contact with the mobile assay reagents (e.g., the enzyme-labelled antibody) for a substantial portion of the assay, and the opportunity for analyte contact with the immobilized analyte capture reagents is present both from forward flow and from reverse flow. Maximizing analyte contact with the assay reagents maximizes the efficiency of analyte capture, facilitating an analytical method which requires only a small volume of test sample and which provides for unusually sensitive detection of even scant quantities of analyte.

Moreover, reversible flow provides a semi-automated format whereby detector reagent may enter the reactive zone following removal of unbound sample and unbound labelled specific binding reagents (e.g., enzyme-antibody conjugate) by wash reagent. This minimizes contact between the detector reagent (e.g., substrate) and unbound labelled specific binding reagents, reducing background (e.g., background color reaction) and, thereby, increasing sensitivity. In addition, the semi-automated format facilitates ease of performance by reducing operator involvement.

The general timing of the reversible immunochromatographic process may be further automated by suitable selection of matrix materials and proper positioning of binding reagents within the matrix. For example, a soluble film may be located at the base of the sample entry port which first directs flow of the sample liquid toward the specific binding reagents; the dissolution of the film (by residual sample in the sample entry cup) then reverses the direction of the capillary flow through the device by allowing contact between an absorbent reservoir (located beneath the film) and the flow matrix. The timed dissolution of this film increases the period available for immunocomplex formation, without requiring precisely-timed addition(s) of one or more reagents by the operator. A second soluble film may be located at the base of the detector/wash dispenser cup(s). Dissolution of this film by sample which has traversed the length of the flow matrix allows contact of the detector/wash with the flow matrix and, upon reversal of the fluid flow and emptying of the flow matrix at the detector/wash entry point, the detector/wash is flowed by capillary action in the direction of the immobilized binding reagents.

In sum, the reversible flow technique of the instant invention facilitates assays which are of low background and high specificity. In addition, the automated nature of the immuno-chromatographic process significantly reduces the level of technical sophistication required of an individual performing the binding assays described herein, facilitating assays which may be carried out in an environment remote from a laboratory and by reasonably untrained practitioners.

DETAILED DESCRIPTION

The drawings will first briefly be described.

Figure 1:
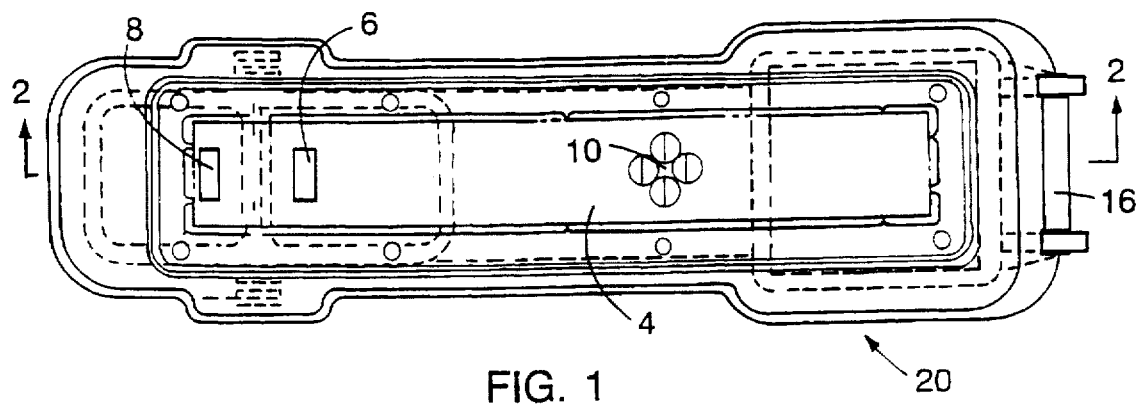
FIG. 1 is a top plan view of a device for carrying out the reversible flow chromatographic binding assay of the present invention.

The present invention features methods and devices for performing specific binding assays on fluid samples suspected of containing analyte molecules. One specific form of the assay method described below is a sandwich format in which sample analyte is contacted with non-immobilized labelled specific binding reagents (e.g., an enzyme-antibody conjugate). The analyte is immobilized (at a detection zone) as a result of its binding to an analyte capture reagent (e.g., analyte-specific antibody bound to a solid substrate, e.g., Latex beads or the assay device itself). Complex formation at the detection zone is assayed either directly (e.g., when using a radioactive, fluorescent, or light-absorbing label) or following reaction with a detector reagent (e.g., a chromogenic substrate which reacts with the enzyme component of an enzyme-antibody conjugate).

Generally, to perform such a binding assay using the methods and devices of the instant invention involves three steps. First, sample containing the analyte is applied to the device via a sample application means and allowed to flow along, and eventually to saturate, the flow matrix. This facilitates sequential complex formation; analyte binds first to the non-immobilized labelled specific binding reagent and then to the immobilized analyte capture reagent. Next, the absorbent reservoir is contacted with the saturated flow matrix (e.g., mechanically or by dissolution of a soluble film which serves to separate the absorbent reservoir from the flow matrix), thereby reversing the fluid flow. Finally, detector and/or wash solution is delivered to the flow matrix (e.g., by piercing a storage vessel containing the solution(s) or by allowing the sample to dissolve a soluble film which serves to separate the liquid reagents from the flow matrix). The liquid reagents remove unbound sample and unbound labelled specific binding reagent and also facilitate detection of analyte complexes (at the location of the immobilized analyte capture reagent). Contact of the flow matrix with the absorbent reservoir and delivery of liquid reagents is preferably performed simultaneously.

The overall sequencing of the above steps is therefore controlled by the flow of the liquid within the flow matrix and the physical positioning of the sample and liquid reagent entry points relative to the position of the deposited labelled specific binding reagents and the analyte capture reagent. Operator involvement is, in general, limited to a maximum of three steps: application of the sample, one-step release of stored liquid reagents (i.e., substrate/wash solution), and mechanical contacting of the absorbent reservoir with the flow matrix. Use of dissolvable films to control absorbent reservoir contact with the flow matrix and/or release of the detector/wash solution(s) reduces opeator involvement to two steps or even a single step.

To facilitate a reversible flow-type binding assay, a device according to the invention generally consists of the following components: a sample entry means; a flow matrix which is capable of supporting capillary liquid flow and which initially directs flow in the forward direction (i.e., away from the sample entry means); an absorbent reservoir positioned adjacent to the sample entry means which may be fluidically coupled to the flow matrix in order to promote liquid flow in the reverse direction (i.e., back toward the sample entry means); and a liquid reagent entry means located at the opposite end of the device which facilitates delivery of a detector reagent and/or a wash reagent upon reversal of the liquid flow.

There now follow descriptions of particular test devices according to the invention. These examples are provided for the purpose of illustrating, not limiting, the invention.

Figure 2A:
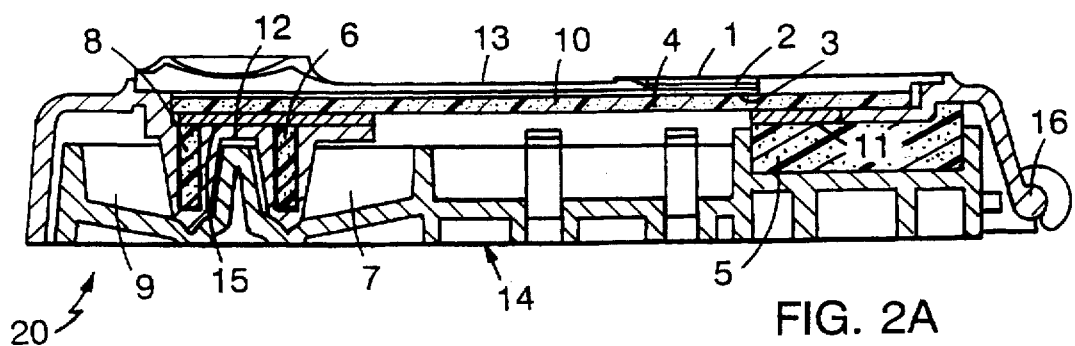
FIG. 2A is a cross-sectional illustration of the device of FIG. 1, showing the position of the top portion after operator activation.
Figure 2B:
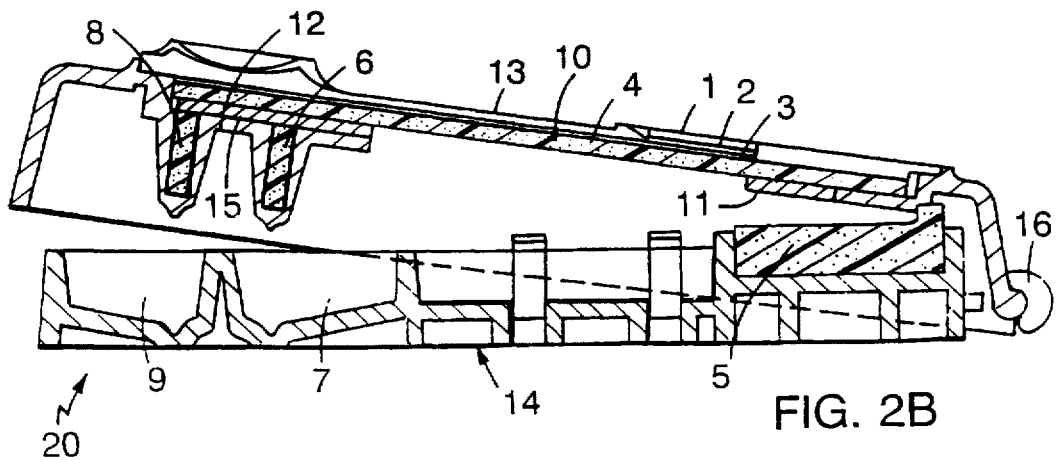
FIG. 2B is a cross-sectional illustration of the device of FIG. 1, showing the position of the top portion before operator activation.

FIGS. 1 and 2 depict one example of a device 20 according to the invention. Components of the device are enclosed within an upper housing portion 13 and a lower housing portion 14, pivotably disposed with respect to each other by means of a hinge 16. Such a housing serves to properly hold the components in place and to allow delivery of a sample to the internal flow matrix as well as to allow an operator to visually monitor assay results. The pivotal connection initially holds the two portions of the housing apart (allowing "forward" flow). Operator activation is accomplished by squeezing components 13 and 14 together, contacting the flow matrix with the absorbent reservoir and releasing the liquid reagents (as described below), enabling "reverse flow".

To carry out a binding assay using such a device, fluid sample is applied through a sample entry cup 1. The fluid sample is drawn into the flow matrix 4 as follows. First, the sample flows through a sample prefilter pad 2 which removes interfering particulate matter and, next, through a labelled specific binding reagent pad 3 upon which labelled specific binding reagent has been deposited and dried. Contact of the labelled specific binding reagent pad with the fluid sample results in dissolution of the labelled specific binding reagent into the sample, allowing sample analyte to bind to the labelled specific binding reagent; positioning of the labelled specific binding reagent pad adjacent to the sample entry cup increases the quantity of sample which contacts the dried reagent. Sample and labelled specific binding reagent are then drawn, by capillary action, into the flow matrix 4 and transported in the "forward" direction within the physical structure of the matrix towards and past the reactive zone 10 where immobilized analyte capture reagent has been incorporated into the flow matrix. At the reactive zone 10, all binding species are present (i.e., sample, labelled specific binding reagent and immobilized analyte capture reagent). Fluid flow continues in the forward direction until the flow matrix 4 is saturated, at which point, fluid flow ceases. At this time, housing components 13 and 14 are squeezed together by the operator (as described above), bringing the flow matrix 4 into contact with the absorbent reservoir 5. The absorbent reservoir is positioned toward one end of matrix 4 so as to draw the fluid out of the matrix and to reverse the direction of fluid flow within the device.

Upon flow reversal, liquid reagents are delivered to the flow matrix. In the device illustrated in FIGS. 1 and 2, such liquid reagents include a wash reagent and a detector reagent. The wash reagent is stored in a wash reagent storage vessel 7 and is delivered, by the wash reagent delivery wick 6 into the flow matrix 4. The purpose of the wash reagent is to transport unbound sample and unbound labelled specific binding reagent along the flow matrix 4 and away from the reactive zone 10. Detector reagent is stored in the detector reagent storage vessel 9 and is delivered, by the detector reagent delivery wick 8 into the flow matrix 4. The detector reagent facilitates analyte detection. The device depicted in FIGS. 1 and 2 illustrates a physical linkage of the delivery wicks within the lance 12 which serves to both pierce the storage vessels and deliver the reagent to the flow matrix. This linkage facilitates the release of the two stored liquid reagents with a single action. Sequential utilization of the two reagents, i.e., wash reagent followed by detector reagent is accomplished by delivering the wash reagent closer to the absorbent reservoir 5 than the detector reagent. Fluid flow toward the absorbent reservoir causes the wash reagent to be pulled into the flow matrix 4 by capillary force. Once the volume of the delivered reagent has been absorbed into the flow matrix, displacing unbound sample and unbound labelled specific binding reagent, detector reagent is delivered into the flow matrix 4 by capillary force. Detector reagent displaces the wash reagent in the direction of the absorbent reservoir 5. When the detector reagent flows into the reactive zone 10, complex formation is detectable, and the assay procedure is complete.

In an alternative device according to the invention, the detector reagent acts both to remove unbound sample and reagents from the reactive zone and to facilitate analyte detection. Such a device may be designed essentially as shown in FIGS. 1 and 2, except that the device includes a single reagent storage vessel and a single reagent delivery wick (e.g., included as a component of the lance). As described above, sample is added to the device and, at some point after addition (and preferably, after sample has saturated the flow matrix), the device is operator activated (as described above). The detector reagent storage vessel is pierced by the lance (containing a delivery wick) and the detector reagent delivered to the flow matrix. Reversal of the fluid flow (also as described above) draws the detector reagent into the flow matrix by capillary force. As the detector reagent flows towards the absorbent reservoir, it displaces the fluid in the flow matrix, clearing the matrix, and importantly, clearing the reactive zone of unbound sample and unbound labelled specific binding reagent.

In the case of a labelled specific binding reagent conjugated to a radioactive, fluorescent, or light-absorbing molecule, the detector reagent acts merely as a wash solution facilitating detection of complex formation at the reactive zone by washing away unbound labelled reagent.

In the case of a specific binding reagent conjugated, e.g., to an enzyme, the detector reagent includes, e.g., a substrate which produces a detectable signal upon reaction with the enzyme-antibody conjugate at the reactive zone. In such a case, a finite quantity of inhibitor reagent may be incorporated into an inhibitor reagent pad located at the junction of the detector reagent dispense cup and the flow matrix or may be dried directly on to the flow matrix between the detector reagent dispense cup and the reactive zone. When the finite quantity of inhibitor migrates out of the reactive zone, detector reagent produces a detectable signal upon contact with the labelled specific binding reagent.

To ensure proper operation, any of the devices described herein may further include various binding reagents immobilized at the reactive zone 10 at positions distinct from the analyte capture reagent(s). For example, an immunoreagent which recognizes the species-specific antibody portion of a labelled specific binding reagent or the enzyme portion of an enzyme-labelled reagent may be included as a positive control to assess the viability of the reagents within the device. Additionally, a reagent, e.g., an antibody isolated from a non-immune member of the species from which the antibody portion of the enzyme-antibody conjugate was derived may be included as a negative control to assess the specificity of immunocomplex formation.

To maximize automation, any of the devices described herein may further include a soluble film 11 which separates the flow matrix 4 from the absorbent reservoir 5. Sample added to the flow matrix at the sample entry port 1 is thereby flowed in a single direction (i.e., away from the absorbent reservoir) maximizing the amount of sample which flows past the reactive zone 10. The film is dissolved slowly by the fluid sample and, upon dissolution, contact occurs between the absorbent pad 5 and the flow matrix 4 and promotes a reversal of the fluid flow. A soluble film 15 may also be positioned between the liquid reagent storage vessels 6 and 8 and the flow matrix. Dissolution of the film by fluid which has flowed to the end of the matrix (i.e., the end distal to the sample entry port 1) allows delivery of the liquid reagents to the flow matrix. Reverse fluid flow draws the reagents into the matrix by capillary force.

The fundamental components of the invention may be packaged as a single unit or housed as several units for multiple-sample devices. Various packaging options in which liquid reagent storage reservoirs or sample entry points are shared between several flow matrix components may also be envisioned. In one particular example, the device contains multiple regions within the reactive zone, each including a different analyte capture reagent (e.g., one may include an immobilized antibody specific for feline immunodeficiency virus and another may include an immobilized antibody specific for feline leukemia virus); a single biological sample (e.g., a sample of feline serum) is assayed for the presence of one or both viruses.

Preferably, the reactive zone 10 is seen from the outside of the housing, allowing ready detection of assay results. The sample entry cup 1 is preferably designed such that the volume of the cup is at least as large as the total volume of sample required to perform the assay. In addition, the absorbent pad 5 is preferably of sufficient size to accommodate the total volume of sample as well as all added liquid reagents (i.e., detector reagent and wash reagent).

The flow matrix material preferably possesses the following characteristics: (1) low non-specific affinity for sample materials and labelled specific binding reagents, (2) ability to transport a liquid by capillary action over a distance with a consistent liquid flow across the matrix, and (3) ready binding to immobilized specific binding reagents, (e.g., by covalent or non-covalent attachment or by physical entrapment). Materials possessing these characteristics include fibrous mats composed of synthetic or natural fibers (e.g., glass or cellulose-based materials or thermoplastic polymers, such as, polyethylene, polypropylene, or polyester); sintered structures composed of particulate materials (e.g., glass or various thermoplastic polymers); or cast membrane films composed of nitrocellulose, nylon, polysulfone or the like (generally synthetic in nature). The invention may utilize a flow matrix composed of sintered, fine particles of polyethylene, commonly known as porous polyethylene; preferably, such materials possess a density of between 0.35 and 0.55 grams per cubic centimeter, a pore size of between 5 and 40 microns, and a void volume of between 40 and 60 percent. Particulate polyethylene composed of cross-linked or ultra high molecular weight polyethylene is preferable. A flow matrix composed of porous polyethylene possesses all of the desirable features listed above, and in addition, is easily fabricated into various sizes and shapes. A particularly preferred material is 10-15 micron porons polyethylene from Chromex Corporation FN# 38-244-1 (Brooklyn, N.Y.).

Materials suitable for use as an absorbent reservoir are preferably highly absorbent, provide capacity in excess of the volume of the fluid sample plus the added liquid reagents, and are capable of absorbing liquids from the flow matrix by physical contact as the sole means of fluid transfer between the two materials. A variety of materials and structures are consistent with these requirements. Fibrous structures of natural and synthetic fibers such as cellulose and derivitized cellulose (e.g., cellulose acetate) are preferred for this use. The fibers of the material may be oriented along a particular axis (i.e., aligned), or they may be random. A preferred embodiment of the invention utilizes non-aligned cellulose acetate fibers of density range 0.1 to 0.3 grams per cubic centimeter and void volume of 60 to 95 percent. A particularly preferred material is American Filtrona Corporation R-13948 Transorb Reservoir (Richmond, Va.).

Materials suitable for use as a labelled reagent deposit pad preferably possess the following properties: (1) high liquid void volume, facilitating an even exposure of the fluid sample to the solid material upon which the labelled binding reagent has been dried, (2) a rapid flow property such that the rate of sample entry into the flow matrix is not governed by the labelled reagent pad, (3) material surface properties which do not adversely affect the efficacy of the deposited specific binding reagents and which allow ready reconstitution of the dried reagents, and (4) ability to establish liquid flow between the absorbent pad and the flow matrix (e.g., compressibility without loss of flow characteristics). In general, materials having the above properties are fibrous structures with low density fiber configurations. Materials composed of synthetic fibers, such as polyester have the advantage of inert surfaces and low density structures. A preferred labelled reagent deposit pad is composed of a random alignment of polyester fibers which are heat-needled into a mat structure with a material density of 2 to 12 ounces of polyester per square yard. A particularly preferred material is Troy Mills polyester mat # 1-9-195 (Troy, N.H.).

The housing is preferably watertight to prevent leakage and is manufactured from an inert material, with polymer materials being preferred for their ease of fabrication.

Materials suitable for use as a dissolvable film are preferably dissolved by the fluid sample, do not interfere with specific binding or chemical reactions necessary to the assay, and do not adversely affect the flow properties of the liquids within the flow matrix. In general, materials having the above properties are polymers of molecular weight 3,000 to 10,000,000, including polyvinyl alcohol, polyethylene oxide, and methyl cellulose. A preferred material for use in the invention is polyvinyl alcohol of thickness 0.0016 inches; such a film is available from Specialty Products (McAdoo, Pa.; Cat. No. sp 5500).

The signal producing system will generally involve the production of a detectable signal, for example, due to a radioactive, fluorescent, or light-absorbing molecule. Such a molecule preferably does not interfere with the ability of the labelled specific binding reagent to traverse the flow matrix. In addition, if the detectable end product is produced upon reaction with detector reagent, it is preferable that end product precipitate out of solution resulting in a localized signal rather than a "lateral streak" which extends throughout the flow matrix. Such a signal producing system may involve an enzyme and a substrate. One example of a substrate which forms an insoluble end product following reaction with the enzyme, alkaline phosphatase, is indoxyl phosphate. An example of a substrate which produces an insoluble end product following reaction with the enzyme, horseradish peroxidase, is TMBlue, available from TSI Incorporated (Worcester, Mass.; Cat. No. TM 101). If the signal producing system involves production.

Alternatively, the signal producing system may involve an enzyme or coenzyme which produces an end-product which absorbs light (e.g., a dye) or which emits light upon irradiation or chemical reaction, i.e., a fluorescent or chemiluminescent molecule, respectively. A large number of enzymes and coenzymes for providing such products are indicated in U.S. Pat. No. 4,275,149 and U.S. Pat. No. 4,318,980 (hereby incorporated by reference). The product of the enzyme reaction will usually be a dye or fluorescer. A large number of illustrative fluorescers are also indicated in U.S. Pat. No. 4,275,149, which is incorporated by reference.

Of particular interest is the enzyme horseradish peroxidase which produces a colored product when reacted with the substrate, 4-chloro-1-napthol. One commercially-available substrate solution is termed TM Blue and is available from TSI Incorporated (Worcester, Mass.). Also of interest are enzymes which involve the production of hydrogen peroxide and the use of the hydrogen peroxide to oxidize a dye precursor to a dye. Particular combinations include saccharide oxidases e.g., glucose and galactose oxidase, or heterocyclic oxidases, such as uricase and xanthine oxidase, coupled with an enzyme which employs the hydrogen peroxide to oxidize a dye precursor, e.g., peroxidase, microperoxidase, and cytochrome C oxidase. Additional enzyme combinations may be found in the subject matter incorporated by reference.

The detector reagent may also serve to remove unbound sample and binding reagents from the flow matrix by inclusion in the detector solution of a limited quantity of inhibitor; such an inhibitor blocks the development of a visible end product. In general, a suitable inhibitor must dissolve quickly and completely into the detector reagent solution. The inhibitor blocks end product development, e.g., by reversibly inhibiting the activity of the enzyme conjugate, by chemically consuming substrate molecules, or by acting as an alternative substrate which produces no visible end product upon reaction with the enzyme.

In particular examples, the enzyme alkaline phosphatase is inhibited by a 0.05M sodium phosphate solution at pH6 to pH7; inhibition is due to decreased enzyme activity (resulting from a solution pH which is lower than alkaline phosphatase's optimum pH of 10). In another example the enzyme horseradish peroxidase is inhibited by 0.025M sodium metabisulfite. In this case, end product formation is blocked because the inhibitor chemically consumes the electron-donating peroxide substrate (i.e., by reducing available substrate). Horseradish peroxidase may also be inhibited by 0.05M ascorbic acid. Ascorbic acid serves as an alternative horseradish peroxidase substrate, reacting with the enzyme but producing no visible end product.

The quantity of added inhibitor is determined empirically. A suitable amount of inhibitor blocks production of end product until most or all of the unbound labelled binding reagent is removed from the reactive zone, at which time, detectable end product is produced.

The methods and devices of the invention facilitate sandwich or competition-type specific binding assays. In the case of a sandwich assay, the specific binding reagent (e.g., the antibody) is immobilized in the reactive zone. Following binding of the sample analyte, the complex is reacted with labelled specific binding reagent (e.g., an enzyme-antibody conjugate) and analyte detected (e.g., upon reaction with substrate). In the case of a competition assay, specific binding reagent (e.g. an antibody) immobilized at the reactive zone is contacted simultaneously with sample analyte and labelled analyte (e.g., an analyte-enzyme conjugate). The amount of label detected at the reactive zone is inversely proportional to the amount of analyte in the sample.

Any or all of the above embodiments may be provided as a kit. In one particular example, such a kit would include a device, e.g., as shown in FIG. 2, complete with specific binding reagents (e.g., a non-immobilized labelled specific binding reagent and an immobilized analyte capture reagent) and wash reagent, as well as detector reagent and positive and negative control reagents, if desired or appropriate. In addition, other additives may be included, such as stabilizers, buffers, and the like. The relative amounts of the various reagents may be varied widely, to provide for concentrations in solution of the reagents which substantially optimize the sensitivity of the assay. Particularly, the reagents may be provided as dry powders, usually lyophilized, which on dissolution will provide for a reagent solution having the appropriate concentrations for combining with the sample.

The present invention is further illustrated by the following example. This example is not limiting to the invention.

EXAMPLE 1

This example relates to the use of the present methods and devices for the detection of Feline Leukemia Virus (FeLV) in a sample.

An immobilized specific binding reagent was produced as follows. Latex microspheres (0.26 micron; amidine latex; Interfacial Dynamics Corporation, Portland, Oreg.) are coated overnight with anti-FeLV antibodies (see, e.g., U.S. Ser. No. 07/219,100; IDEXX Corporation, Portland, Me.) at 3 mg/ml by the method described in *Microparticle Immunoassay Techniques* (a publication of Seradyn, Inc., Particle Technology Division, Indianapolis, Ind.). Specifically, the microspheres were first washed with 0.01M potassium phosphate (pH 7.2) and then overcoated with 1% (w/v) bovine serum albumin (BSA) in 0.01M potassium phosphate (pH 7.2) for one hour. The microspheres were washed a second time and then resuspended in 0.01 M potassium phosphate (pH 7.2) and 1% (w/v) sucrose at a concentration of approximately 1% (w/v) latex microspheres. One to two microliters of the anti-FeLV-coated microspheres were spotted onto a strip of 10–15 micron porous polyethylene (1 cm×5 cm×0.16 cm; Chromex Corporation, Brooklyn, N.Y.) and dried at 37° C. for 30 minutes; this flow matrix was stored desiccated.

To produce the labelled specific binding reagent, anti-FeLV p24 antibody was covalently coupled to horseradish peroxidase (see e.g., U.S. Ser. No. 07/219,100; IDEXX Corp., Portland, Me.). Two hundred and fifty microliters of a solution containing 2 to 10 micrograms of this conjugate was added to the labelled reagent deposit pad, i.e., a polyester pad 1 cm in diameter×0.635 cm thick (Troy Mills, Troy, N.H., #1-9-195). The pad was vacuum-dried for one hour and stored desiccated.

The porous polyethylene flow matrix and the labelled reagent deposit pad were assembled into a device resembling that illustrated in FIGS. 1 and 2. Two hundred and fifty microliters of sample were added to the sample cup; the sample consisted of feline serum which had previously tested negative for the presence of FeLV and to which was added 5-10 nanograms of disrupted FeLV. 300 microliters of a wash solution (i.e., 0.3% Tween 80, 0.3% Triton X-100 and 5% bovine serum albumin) and 500 microliters of horseradish peroxidase substrate solution (i.e., a stable organic peroxide which precipitates upon reaction with horseradish peroxidase, e.g., TMBlue #TM101, TSI, Incorporated, Worcester, Mass.) were stored in the wash reagent storage vessel and detector reagent storage vessel, respectively.

Sample flow into the labelled reagent deposit pad dissolved the dried enzyme conjugate, facilitating complex formation between FeLV p24 in the sample and the anti-p24 antibody-horseradish peroxidase conjugate. Sample flow through the reactive zone (i.e., the position where the anti-p24 antibody-coated latex microspheres had been deposited) then facilitated immunocomplex formation between the immobilized anti-p24 antibody, the sample FeLV p24, and the anti-p24 antibody-horseradish peroxidase conjugate; such immune complexes were immobilized on the microspheres. Upon saturation of the flow matrix (i.e., when the volume of added sample occupied a void volume equivalent to the flow matrix), the flow matrix was manually contacted with the absorbent reservoir (i.e., by squeezing the two "halves" of the device together as described above). This operation also served to puncture the foil sealing the wash reagent and detector reagent storage vessels, allowing sequential delivery of the wash reagent and the detector reagent into the flow matrix. Unbound sample and unbound antibody-horseradish peroxidase conjugate were displaced by the wash reagent. Subsequently, the TMBlue detector substrate was oxidized by the immobilized horseradish peroxidase conjugate forming a detectable colored product. The presence or amount of colored product formed was proportional to the level of FeLV antigen present in the sample.

In this particular example, the device was used clinically to quickly and easily diagnose cats for the presence of the FeLV p24 antigen (i.e., for detection of feline leukemia virus infection). The device may be used, in a similar manner, to detect other analytes of choice. Such analytes include the gp130 protein of feline immunodeficiency virus (see, e.g., U.S. Ser. No. 07/447,810), the envelope protein of a human immunodeficiency virus, or an antigen of canine heartworm (i.e., one derived from *Dirofilarta immitis*; see, e.g., Weil, U.S. Pat. No. 4,839,275).

I claim:

1. A device for performing an assay which determines the presence or quantity of an analyte in a fluid sample by detecting binding of said analyte to at least one immobilized analyte capture reagent after washing unbound material from said immobilized analyte capture reagent, said device comprising:

(a) an elongated solid phase flow matrix, said flow matrix comprising capillary channels capable of driving capillary fluid movement, said flow matrix further comprising
       i) a first region adapted for receipt of said fluid sample,
       ii) a second region at which said analyte capture reagent is immobilized,
       iii) a third region for application of a liquid detector reagent capable of removing unbound substances from said second region;
    said second region being positioned intermediate to said first region and said third region;

(b) an absorbent reservoir of high volume capacity, wherein, prior to use of said device, said absorbent reservoir is not in fluidic contact with said flow matrix; said device further comprising means for establishing fluidic contact between said absorbent reservoir and said flow matrix at a position selected so that said second region is between said absorbent reservoir and said third region;

(c) a sealed container of said liquid detector reagent positioned to be introduced at said third region of said matrix;

whereby said flow matrix and said regions thereof are sized and positioned to cause said fluid sample to flow initially along said elongated flow matrix in one direction toward and through said second region, and subsequently, upon introduction of said liquid detector reagent into the third region of said flow matrix, said liquid detector reagent to flow along said elongated flow matrix in a second direction opposite said first direction, through said second region, and into said absorbent reservoir, drawing unbound substances with it.

2. The device of claim 1, comprising reagents which undergo a detectable reaction as a means to detect analyte bound at said second region, and said liquid reagent comprises a predetermined limited quantity of an inhibitor of said detectable reaction, whereby flow of said liquid reagent transports said inhibitor initially to said second region, and when said inhibitor and unbound substances are transported away from said second region, said detectable reaction takes place in the absence of said unbound substances.

3. The device of claim 1, wherein said analyte is a viral antigen.

4. The device of claim 3, wherein said viral antigen is derived from a human immunodeficiency virus.

5. The device of claim 3, wherein said viral antigen is derived from a feline leukemia virus.

6. The device of claim 1, wherein said analyte is derived from *Dirofilaria immitis*.

7. The device of claim 1, wherein, prior to use of said device, said absorbent reservoir is positioned so as not to contact said flow matrix, and said device further comprising means for moving said absorbent reservoir into fluidic contact with said flow matrix.

8. The device of claim 1, said device further comprising a housing containing: (a) said elongated flow matrix; (b) said sealed container of said liquid reagent; and (c) means for applying said liquid reagent from said container to said third region of said flow matrix.

9. The device of claim 8, wherein said means for applying said liquid reagent to said flow matrix comprises a lance positioned and adapted to pierce said container.

10. The device of claim 7 comprising a housing containing: (a) said elongated flow matrix; (b) said sealed container of said liquid reagent; and (c) means for applying said liquid reagent from said container to said third region of said flow matrix, said means for moving said absorption reservoir into fluidic contact with said flow matrix being connected to said means for applying said liquid reagent, whereby an operator activates both said means in a single operation.

11. The device of claim 1, wherein said liquid reagent is a wash reagent and said flow matrix further comprises a fourth region for the application of a detector reagent, said third region being positioned intermediate to said second region and said fourth region.

12. The device of claim 11, said device comprising at least two sealed storage containers, one of said sealed storage containers containing a wash reagent, and the other of said sealed storage containers containing said liquid detector reagent, both of said sealed containers being positioned proximal to said fourth region of said flow matrix.

13. The device of claim 12, wherein said device further includes a means for applying said detector reagent and a means for applying said wash reagent, and said means for applying said detector reagent is connected to said means for applying said wash reagent, whereby an operator applies both said detector reagent and said wash reagent in a single operation.

14. The device of claim 13, wherein said means for applying said detector reagent and said wash reagent comprises a lance positioned and adapted to pierce both said containers.

15. The device of claim 1, said device further comprising at least one barrier comprising a soluble member positioned to block flow of said liquid reagent to said absorbent reservoir, whereby dissolution of said solid member permits fluid flow of said liquid reagent in said second direction to said absorbent reservoir after a predetermined time selected to be sufficient to permit sample to flow in said first direction through said second region.

16. The device of claim 15, wherein said barrier is positioned between said first region and said absorbent reservoir.

17. The device of claim 15, wherein said barrier is positioned between said third region and said second region.

18. The device of claim 15, comprising two of said barriers, one of said barriers being positioned between said first region and said absorbent reservoir, the second of said barriers being positioned between said third region and said second region.

19. A method for performing an assay which determines the presence or quantity of an analyte in a fluid sample by detecting binding of said analyte to at least one immobilized analyte capture reagent after washing unbound material from said immobilized analyte capture reagent, said method comprising:
(a) providing
(i) an elongated solid phase flow matrix, said flow matrix comprising capillary channels capable of driving capillary fluid movement, said flow matrix further comprising
a) a first region adapted for receipt of said fluid sample,
b) a second region at which said analyte capture reagent is immobilized,
c) a third region for application of a liquid detector reagent capable of removing unbound substances from said second region; said second region being positioned intermediate to said first region and said third region;
(ii) an absorbent reservoir of high volume capacity, wherein, prior to performing said method, said absorbent reservoir is not in fluidic contact with said flow matrix;
(b) applying said fluid sample to said first region of said flow matrix;
(c) allowing said fluid sample to flow in a first direction through said second region, and then introducing said liquid detector reagent into said flow matrix at said third region;
(d) moving said absorbent reservoir into fluidic contact with said flow matrix, such that said sample and said liquid detector reagent flow in a second direction, opposite to said first direction; and (e) detecting said analyte bound at said second region.

20. The method of claim 19, wherein said analyte bound at said second region is detected by reagents which undergo a detectable reaction, and said liquid reagent comprises a predetermined limited quantity of an inhibitor of said detectable reaction, whereby flow of said liquid reagent transports said inhibitor initially to said second region, and, when said inhibitor and unbound substances are transported away from said second region, said detectable reaction takes place in the absence of said unbound substances.

21. The method of claim 19, wherein said analyte is a viral antigen.

22. The method of claim 21, wherein said viral antigen is derived from a human immunodeficiency virus.

23. The method of claim 21, wherein said viral antigen is derived from a feline leukemia virus.

24. The method of claim 19, wherein said analyte is derived from *Dirofilaria immitis*.

25. The method of claim 19, wherein, prior to use of said method, said absorbent reservoir is positioned so as not to contact said flow matrix, and after said fluid sample flows in a first direction through said second region, said absorbent reservoir is moved into fluidic contact with said flow matrix such that said sample and said liquid reagent flow in a second direction opposite to said first direction, through said second region, and into said absorbent reservoir, drawing unbound substances with it.

26. The method of claim 19, wherein said liquid reagent is contained in a sealed container and is applied to said third region of said flow matrix by piercing said container.

27. The method of claim 25, wherein said absorbent reservoir is brought into fluidic contact with said flow matrix and said liquid reagent is applied to said third region of said flow matrix by a single operator action.

28. The method of claim 19 or 20, wherein said liquid reagent is a wash reagent and said flow matrix further comprises a fourth region for the application of a detector reagent, said third region being positioned intermediate to said second region and said fourth region.

29. The method of claim 28, wherein said wash reagent and said detector reagent are each contained in separate sealed containers and are applied to said flow matrix by simultaneously piercing each of said containers with at least one lance.

30. The method of claim 19, said method further comprising providing at least one barrier comprising a soluble member positioned to block flow of said liquid reagent to said absorbent reservoir, whereby dissolution of said solid member permits fluid flow of said liquid reagent in said second direction to said absorbent reservoir after a predetermined time selected to be sufficient to permit sample to flow in said first direction through said second region.

31. The method of claim 30, wherein said barrier is positioned between said first region and said absorbent reservoir.

32. The method of claim 30, wherein said barrier is positioned between said third region and said second region.

33. The method of claim 30, comprising two of said barriers, one of said barriers being positioned between said first region and said absorbent reservoir, the second of said barriers being positioned between said third region and said second region.

34. A device for performing an assay which determines the presence or quantity of an analyte in a fluid sample by detecting binding of said analyte to at least one immobilized analyte capture reagent after washing unbound material from said immobilized analyte capture reagent, said device comprising:

(a) an elongated fluid flow matrix comprising, (1) a first segment for receiving a fluid sample, (2) a second region at which analyte capture reagents are immobilized, (3) a third region for application of a liquid detector reagent capable of removing unbound substances from said second region, (b) an absorbent reservoir of high volume capacity, (c) a sealed container of said liquid detector reagent positioned to be introduced at said third region of said flow matrix, (d) at least one soluble barrier positioned to block flow of said liquid detector reagent from said container to said absorbent reservoir, said second region being positioned intermediate to said third region and said absorbent reservoir, said soluble barrier blocking flow of said liquid detector reagent to said absorbent reservoir until after said sample has flowed from said first region through said second region, at which point said barrier dissolves permitting said liquid detector reagent to flow in said wash path.

35. The device of claim 34, wherein said barrier is positioned between said liquid reagent container and said second region.

36. The device of claim 34 or 35, wherein said barrier is positioned between said first region and said absorbent reservoir.

* * * * *